US007323184B2

(12) United States Patent
Freddo et al.

(10) Patent No.: US 7,323,184 B2
(45) Date of Patent: Jan. 29, 2008

(54) COMPOSITIONS AND METHODS FOR THE TREATMENT OF WOUNDS AND THE REDUCTION OF SCAR FORMATION

(75) Inventors: Mary Ellen Freddo, Monson, MA (US); Ki Chang Keum, Seoul (KR); Naechoon Yoo, Seoul (KR); Won Min Yoo, Seoul (KR)

(73) Assignee: Healagenics, Inc., Woburn, MA (US)

( * ) Notice: Subject to any disclaimer, the term of this patent is extended or adjusted under 35 U.S.C. 154(b) by 0 days.

(21) Appl. No.: 11/476,543

(22) Filed: Jun. 28, 2006

(65) Prior Publication Data

US 2007/0059377 A1    Mar. 15, 2007

Related U.S. Application Data

(63) Continuation-in-part of application No. 11/210,619, filed on Aug. 23, 2005.

(51) Int. Cl.
*A61K 9/00* (2006.01)
*A61K 9/50* (2006.01)
*A61K 33/00* (2006.01)
*A01N 43/04* (2006.01)

(52) U.S. Cl. .............. 424/400; 424/520; 424/600; 514/55.1

(58) Field of Classification Search .......... 424/400, 424/422, 426, 434, 520
See application file for complete search history.

(56) References Cited

U.S. PATENT DOCUMENTS

| 4,141,973 | A | * | 2/1979 | Balazs ................ 514/54 |
| 4,659,572 | A | | 4/1987 | Murray |
| 4,808,576 | A | | 2/1989 | Schultz et al. |
| 4,842,305 | A | | 6/1989 | Kistenich et al. |
| 4,851,521 | A | | 7/1989 | della Valle et al. |

(Continued)

FOREIGN PATENT DOCUMENTS

CN    1156042 A    8/1997

(Continued)

OTHER PUBLICATIONS

Arm & Hammer, "Arm & Hammer Dental Care toothpaste was introduced nationally in 1988," *Arm & Hammer Milestones 150th Anniversary*, pp. 8 of 9 (1996). Online. Internet. Accessed on Nov. 8, 2006. <http://www.churchdwight.com/contact/downloads/cd150.pdf>.

(Continued)

*Primary Examiner*—Sharmila Gollamudi Landau
(74) *Attorney, Agent, or Firm*—King & Spalding (57) ABSTRACT

The present invention relates to methods and compositions for inhibiting scar formation on wound region. In certain embodiments, the methods include administering an alkalinization agent in combination with hyaluronic acid to a wound site to reduce the formation of scars at the wound site. Suitable alkalization agents include sodium bicarbonate, sodium hydroxide and potassium hydroxide.

9 Claims, 7 Drawing Sheets

U.S. PATENT DOCUMENTS

| | | | |
|---|---|---|---|
| 4,920,104 A | 4/1990 | DeVore et al. | |
| 4,937,254 A | 6/1990 | Sheffield et al. | |
| 4,937,270 A | 6/1990 | Hamilton et al. | |
| 5,017,229 A | 5/1991 | Burns et al. | |
| 5,080,893 A | 1/1992 | Goldberg et al. | |
| 5,095,037 A | 3/1992 | Iwamitsu et al. | |
| 5,166,331 A | 11/1992 | della Valle et al. | |
| 5,190,759 A | 3/1993 | Lindblad et al. | |
| 5,196,185 A | 3/1993 | Silver et al. | |
| 5,209,724 A | 5/1993 | Dhaliwal et al. | |
| 5,234,914 A | 8/1993 | Gallina | |
| 5,236,906 A | 8/1993 | Yamamoto | |
| 5,356,683 A | 10/1994 | Egolf et al. | |
| 5,358,973 A | 10/1994 | Lindblad et al. | |
| 5,376,365 A | 12/1994 | Dikstein | |
| 5,409,904 A | 4/1995 | Hecht et al. | |
| 5,432,167 A | 7/1995 | Brismar | |
| 5,510,418 A * | 4/1996 | Rhee et al. | 525/54.2 |
| 5,520,926 A | 5/1996 | Ferguson | |
| 5,529,987 A | 6/1996 | Gallina | |
| 5,532,221 A | 7/1996 | Huang et al. | |
| 5,550,112 A | 8/1996 | Gallina | |
| 5,583,120 A | 12/1996 | Gallina | |
| 5,604,200 A | 2/1997 | Taylor-McCord | |
| 5,614,506 A | 3/1997 | Falk et al. | |
| 5,624,915 A | 4/1997 | Gallina | |
| 5,631,011 A | 5/1997 | Wadstrom | |
| 5,631,241 A | 5/1997 | della Valle et al. | |
| 5,631,242 A | 5/1997 | Gallina | |
| 5,639,738 A | 6/1997 | Falk et al. | |
| 5,663,160 A | 9/1997 | Meybeck et al. | |
| 5,681,825 A | 10/1997 | Lindqvist et al. | |
| 5,728,391 A | 3/1998 | Ikeya et al. | |
| 5,731,298 A | 3/1998 | Reinmuller | |
| 5,763,399 A | 6/1998 | Lee | |
| 5,792,753 A | 8/1998 | Falk et al. | |
| 5,811,410 A | 9/1998 | Falk et al. | |
| 5,817,642 A | 10/1998 | Falk et al. | |
| 5,824,658 A | 10/1998 | Falk et al. | |
| 5,827,834 A | 10/1998 | Falk et al. | |
| 5,830,882 A | 11/1998 | Falk et al. | |
| 5,834,444 A | 11/1998 | Falk et al. | |
| 5,852,002 A | 12/1998 | Falk et al. | |
| 5,866,554 A | 2/1999 | Shalaby et al. | |
| 5,910,489 A | 6/1999 | Falk et al. | |
| 5,914,322 A | 6/1999 | Falk et al. | |
| 5,925,626 A | 7/1999 | della Valle et al. | |
| 5,942,498 A | 8/1999 | Falk et al. | |
| 5,962,433 A | 10/1999 | Falk et al. | |
| 5,972,906 A | 10/1999 | Asculai et al. | |
| 5,977,088 A | 11/1999 | Harper et al. | |
| 5,985,850 A | 11/1999 | Falk et al. | |
| 5,990,095 A | 11/1999 | Falk et al. | |
| 5,990,096 A | 11/1999 | Asculai et al. | |
| 6,010,692 A | 1/2000 | Goldberg et al. | |
| 6,017,900 A | 1/2000 | Falk et al. | |
| 6,022,866 A | 2/2000 | Falk et al. | |
| 6,037,331 A | 3/2000 | Shalaby et al. | |
| 6,048,844 A | 4/2000 | Falk et al. | |
| 6,063,406 A | 5/2000 | Hornack | |
| 6,069,135 A | 5/2000 | Falk et al. | |
| 6,086,907 A | 7/2000 | Goldberg et al. | |
| 6,087,344 A | 7/2000 | Falk et al. | |
| 6,096,727 A | 8/2000 | Kuo et al. | |
| 6,103,704 A | 8/2000 | Falk et al. | |
| 6,114,314 A | 9/2000 | Falk et al. | |
| 6,120,804 A | 9/2000 | Drizen et al. | |
| 6,136,793 A | 10/2000 | Falk et al. | |
| 6,140,312 A | 10/2000 | Falk et al. | |
| 6,147,059 A | 11/2000 | Falk et al. | |
| 6,194,392 B1 | 2/2001 | Falk et al. | |
| 6,218,373 B1 | 4/2001 | Falk et al. | |
| 6,232,303 B1 | 5/2001 | Callegaro et al. | |
| 6,251,876 B1 | 6/2001 | Bellini et al. | |
| 6,262,020 B1 | 7/2001 | Lezdey et al. | |
| 6,271,216 B1 | 8/2001 | Mello et al. | |
| 6,294,202 B1 | 9/2001 | Burns et al. | |
| 6,335,034 B1 | 1/2002 | Drizen et al. | |
| 6,387,407 B1 | 5/2002 | Drizen et al. | |
| 6,495,148 B1 | 12/2002 | Abbiati | |
| 6,509,322 B2 | 1/2003 | Benedetti et al. | |
| 6,541,460 B2 | 4/2003 | Petito | |
| 6,573,249 B2 | 6/2003 | Lezdey et al. | |
| 6,596,703 B1 | 7/2003 | Seed et al. | |
| 6,627,620 B1 | 9/2003 | Nielsen | |
| 6,635,267 B1 | 10/2003 | Miyoshi et al. | |
| 6,699,471 B2 | 3/2004 | Radice et al. | |
| 6,723,345 B2 | 4/2004 | Drizen et al. | |
| 6,828,308 B2 | 12/2004 | Mastradonato et al. | |
| 6,838,448 B2 | 1/2005 | Ponzin | |
| 6,924,273 B2 | 8/2005 | Pierce | |
| 7,132,412 B2 | 11/2006 | Petrigni et al. | |
| 7,157,080 B2 | 1/2007 | Radice et al. | |
| 2002/0025921 A1 | 2/2002 | Petito et al. | |
| 2002/0031555 A1 | 3/2002 | Siamon | |
| 2002/0068716 A1 | 6/2002 | Pierce | |
| 2002/0151466 A1 | 10/2002 | Hubbard et al. | |
| 2002/0173485 A1 | 11/2002 | Mastradonato et al. | |
| 2003/0124197 A1 | 7/2003 | Signore et al. | |
| 2003/0180390 A1 | 9/2003 | Keum et al. | |
| 2003/0187381 A1 | 10/2003 | Greenawalt et al. | |
| 2003/0211166 A1 | 11/2003 | Yamamoto et al. | |
| 2003/0212005 A1 | 11/2003 | Petito et al. | |
| 2004/0019011 A1 | 1/2004 | Falk et al. | |
| 2004/0092482 A1 | 5/2004 | Gupta | |
| 2004/0180622 A1 | 9/2004 | Grafton | |
| 2004/0192643 A1 | 9/2004 | Pressato et al. | |
| 2004/0242535 A1 | 12/2004 | Court et al. | |
| 2004/0254143 A1 | 12/2004 | Mastradonato et al. | |
| 2005/0136126 A1 | 2/2005 | Keum et al. | |
| 2005/0107330 A1 | 5/2005 | Greve et al. | |
| 2005/0129622 A1 | 6/2005 | Rault et al. | |
| 2005/0136122 A1 | 6/2005 | Sadozai et al. | |
| 2005/0142161 A1 | 6/2005 | Freeman et al. | |
| 2005/0142208 A1 | 6/2005 | You et al. | |
| 2005/0147679 A1* | 7/2005 | Petito et al. | 424/484 |
| 2005/0180938 A1 | 8/2005 | Novelli | |
| 2005/0181025 A1 | 8/2005 | Velebny et al. | |
| 2005/0182022 A1 | 8/2005 | Pierce | |
| 2005/0220882 A1 | 10/2005 | Pritchard et al. | |
| 2005/0234011 A1 | 10/2005 | Mazzone et al. | |
| 2005/0234013 A1 | 10/2005 | Parsons | |
| 2005/0267068 A1 | 12/2005 | Back et al. | |
| 2005/0272695 A1 | 12/2005 | Bach et al. | |
| 2006/0040895 A1 | 2/2006 | Thacker | |
| 2006/0069064 A1 | 3/2006 | Khaldoyanidi | |
| 2006/0105991 A1 | 5/2006 | Ishikawa et al. | |
| 2006/0122147 A1 | 6/2006 | Wohlrab | |
| 2006/0135469 A1 | 6/2006 | Miyata et al. | |
| 2006/0147393 A1 | 7/2006 | Macchi | |
| 2006/0153893 A1 | 7/2006 | Matsuno et al. | |
| 2006/0188578 A1 | 8/2006 | Fernandez et al. | |
| 2006/0194759 A1 | 8/2006 | Eidelson | |
| 2006/0293257 A1 | 12/2006 | Rosenbloom | |
| 2007/0003505 A1 | 1/2007 | Carey | |
| 2007/0048391 A1 | 3/2007 | Keum et al. | |
| 2007/0059377 A1 | 3/2007 | Freddo et al. | |

FOREIGN PATENT DOCUMENTS

| | | |
|---|---|---|
| CN | 1270812 A | 5/2000 |
| EP | 0497724 A1 | 8/1992 |
| FR | 2770779 A1 | 5/1999 |
| WO | WO 93/08811 A1 | 5/1993 |

| WO | WO02/30432 | * | 4/2002 |
| WO | WO 02/30432 A1 | | 4/2002 |
| WO | WO 03/094937 A1 | | 11/2003 |

OTHER PUBLICATIONS

Baroni, E.A., et al., "Sodium bicarbonate treatment reduces renal injury, renal production of Transforming Growth Factor-β, and Urinary Transforming Growth Factor-β excretion in rats with doxorubicin-induced nephropathy," *Am. J. Kidney Diseases*, 34(2):328-337 (Aug. 1999).

Border, W.A., et al., "Transforming Growth Factor-β in disease: The dark side of tissue repair," *J. Clin. Invest.*, 90:1-7 (Jul. 1992).

Brown, P.D., et al., "Physicochemical activation of recombinant latent transforming growth factor-beta's 1, 2, and 3," *Growth Factors*, 3(1):35-43 (1990).

Fuchs, T., et al., ["Dirt tattooing following an explosion in a chemistry class,"] *Derm. Beruf Umwelt* [*Occupational and Environmental Dermatoses*], 32(4):138-140 (1984) (Provided as English-language abstract).

Jullien, P., et al., "Acidic cellular environments: Activation of latent TGF-β and sensitization of cellular responses to TGF-β and EGF," *Int. J. Cancer*, 43(5):886-891 (May 15, 1989) (Provided as abstract).

* cited by examiner

COMPOSITIONS AND METHODS FOR THE TREATMENT OF WOUNDS AND THE REDUCTION OF SCAR FORMATION

CROSS REFERENCE TO RELATED APPLICATIONS

This application is a continuation-in-part of U.S. application Ser. No. 11/210,619, filed Aug. 23, 2005, the disclosure of which is incorporated herein by reference. This application also claims the benefit of priority to Korean Patent Application No. 10-2005-0076935, filed Aug. 22, 2005.

TECHNICAL FIELD

The present invention relates compositions comprising hyaluronic acid for the treatment of wounds, and the reduction of scar formation on a wound region.

BACKGROUND

Methods for the treatment of wounds have been developed in the art. U.S. Application No. 2003/0180390, published Sep. 25, 2003 and U.S. Application No. 2005/0136126, published Jun. 23, 2005, describe the reduction of scar formation by injecting sodium bicarbonate at the site of the wound to directly control the pH of the wound site and to inactivate TGF-β. These applications disclose alkalinization of the wound region to inactivate TGF-β, thereby to inhibit scar formation.

U.S. Pat. No. 5,731,298 discloses that cross-linked hyaluronic acid may be used for treatment of scars. U.S. Pat. No. 5,209,724, issued May 11, 1993, discloses the use of an anesthetic comprising NaHCO$_3$ for reducing pain. U.S. Pat. No. 6,063,406, issued May 16, 2000 discloses skin care compositions comprising sodium bicarbonate.

U.S. Pat. No. 5,731,298, issued Mar. 24, 1998 describes a method and a pharmaceutical composition for non-topical wound, scar and keloid treatment which contains cross-linked glycosaminoglycans. The formulation can be administered by injection in the form of a gel which contains water.

U.S. Pat. No. 6,048,844, issued Apr. 11, 2000, discloses a combination for administration to a mammal comprising a medicinal agent and hyaluronic acid to facilitate the agent's penetration through the tissue, including scar tissue at the site to be treated through the cell membrane.

There is a need for compositions that can be used to treat wounds and to reduce the formation of scars. There is a need for improved methods of reducing scar formation.

SUMMARY

The present invention provides methods and compositions for the treatment of wounds and scars, such as hypertrophic and keloid scars. New and existing scars can be treated, as well as wounds prior to scar formation. The compositions can be used as an aid in the natural healing process, to allow reduction of scar formation in a wound region.

In particular embodiments, the method includes inducing alkalinization of a wound site, using compositions that are clinically easy to apply. More particularly, an alkalinizing agent is provided for reducing scar formation which can be administered to the dermis tissue of a wound site, increasing the pH of a wound site to induce an alkalinization of the wound site thereby inhibiting the scar formation on the wound site. In addition, a method for reducing scar formation on a wound site is provided comprising administering to the wound site an effective amount of an alkalinizing agent to alkalinize the wound site, and hyaluronic acid, and allowing the wound site to heal thereby reducing scar formation on the healing site. Examples of alkalinizing agents include sodium bicarbonate, sodium hydroxide and potassium hydroxide. Alkalinization of the wound site, together with administration of hyaluronic acid to the wound site, can permit healing of the wound site with reduced scar formation.

In one embodiment, a composition is provided that comprises an alkalinizing agent and hyaluronic acid and has an alkaline pH. In particular embodiments, the compositions comprise an alkalinizing agent and hyaluronic acid optionally with a pharmaceutically acceptable carrier or diluent. Thus, using the methods and compositions described herein, an alkalinizing agent and hyaluronic acid can be administered to the dermis tissue of a wound site to reduce scar formation. The resulting increase in the pH of a wound site to induce an alkalinization of the wound site, permits inactivation of TGF-β, thereby inhibiting scar formation on the wound site. The wound site is allowed to heal, thereby reducing scar formation on the healing site. Non-limiting examples of alkalinizing agents include sodium bicarbonate, sodium hydroxide and potassium hydroxide.

The administration to a wound site of hyaluronic acid and an alkalinizing agent to alkalinize the wound site and inactivate TGF-β can advantageously result in reduced scar formation. Hyaluronic acid compositions having alkaline pHs can inhibit of scar formation with improved results in comparison with hyaluronic acid compositions having a pH less than 7 or an alkalinizing agent individually. In some embodiments, a synergistic effect in inhibition of scar formation is obtained.

A pharmaceutical composition for inhibition of scar formation on a wound region in one embodiment consists essentially of, or comprises, an aqueous solution of an alkalinizing agent and hyaluronic acid which has an alkaline pH. Representative examples of the alkalinizing agent include, but are not limited to, sodium bicarbonate, sodium hydroxide and potassium hydroxide. Other alkalinizing agents include tromethamine (THAM), acetazolamide (Diamox), sodium citrate, potassium citrate, potassium phosphate, dibasic sodium phosphate, tribasic sodium phosphate, and sodium lactate.

The pH of the composition is, for example, about 8.0 to 10; or about 8.0 to 9.0, or is e.g., about 8.5. In another embodiment, the pH of the pharmaceutical composition is between 9.2 and 9.8. The composition may be formulated into various forms, such as injection, ointment, gel, cream, liquid and suspensions.

In one embodiment, the concentration of hyaluronic acid in said pharmaceutical composition is between 0.5% to 5% (wt./wt.). In another embodiment, the concentration of hyaluronic acid is between 1.0% to 3.0%. In another embodiment, the concentration of hyaluronic acid is between 1.0% to 2.0%. In yet another embodiment, the concentration of hyaluronic acid in an aqueous solution is 1.5%+/−0.5% sodium hyaluronate (wt./wt.). The composition is for example an aqueous solution comprising hyaluronic acid.

The pharmaceutical compositions may be administered in a pharmaceutically acceptable carrier. In one embodiment, the carrier may be suitable for intradermal delivery. In another embodiment, the carrier may be suitable for subcutaneous delivery. In still another embodiment, the pharmaceutical carrier may be suitable for topical delivery.

DETAILED DESCRIPTION

Provided are pharmaceutical compositions and methods for inhibiting scar formation, for example, in a wound region. In one embodiment, the composition comprises an alkalinizing agent and hyaluronic acid optionally in a pharmaceutically acceptable carrier, and the composition has an alkaline pH. New and existing scars can be treated, as well as wounds prior to scar formation. The compositions can be used as an aid in the natural healing process, to allow reduction of scar formation, for example, in a wound region.

In one embodiment, a method for reducing scar formation is provided, the method comprising administering hyaluronic acid and an alkalinizing agent, together or in alternation, to the dermis tissue of a wound site, to increase the pH of a wound site, and to induce an alkalinization of the wound site. This can result in inactivation of TGF-β, thereby inhibiting the scar formation on the wound site. The wound site is allowed to heal, thereby reducing scar formation on the healing site.

Representative examples of the alkalinizing agent include, but are not limited to, sodium bicarbonate, sodium hydroxide and potassium hydroxide. Other alkalinizing agents include tromethamine (THAM), acetazolamide (Diamox), sodium citrate, potassium citrate, potassium phosphate, dibasic sodium phosphate, tribasic sodium phosphate, and sodium lactate.

The pH of the composition is, for example, about 8.0 to 10.0; about 8.0 to 9.0; or e.g., about 8.5. In another embodiment, the pH of the pharmaceutical composition is between 9.2 and 9.8. The composition may be formulated into various forms, such as a solution for injection, or an ointment, a gel, a cream, a liquid or a suspension for topical administration.

Hyaluronic acid is a linear polysaccharide with a molecular weight range of for example, about 50,000 to 8,000,000 Daltons. Hyaluronic acid is commercially available and can be prepared, e.g., from Streptococcus pyogenes bacteria by fermenting the bacteria under anaerobic conditions followed by centrifugation, filtration and other purification steps.

Hyaluronic acid of any molecular weight can be used in the methods and compositions disclosed herein. The hyaluronic acid is, for example, molecular weight of about 400,000 to 4 million Daltons; about 500,000 to 2 million Daltons, about 700,000 to 2,000,000 Daltons or about 760,000 to 2,000,000 Daltons. In particular embodiments, the molecular weight of the hyaluronic acid is at least about 700,000; 750,000; 760,000; 770,000; 780,000; 790,000; or 800,000 Daltons or more. Additionally lower molecular weight hyaluronic acid may be used, such as about 70,000 to 500,000 Daltons.

In one embodiment, the concentration of hyaluronic acid in the pharmaceutical composition is about 0.5% to 5% (wt./wt.). In another embodiment, the concentration of hyaluronic acid is about 1.0% to 3.0% (wt./wt.). In another embodiment, the concentration of hyaluronic acid is about 1.0% to 2.0% (wt./wt.). In yet another embodiment, the concentration of hyaluronic acid is about 1.5% (wt./wt.).

The pharmaceutical compositions may be administered in a pharmaceutically acceptable carrier. In one embodiment, the carrier may be suitable for intradermal delivery. In another embodiment, the carrier may be suitable for subcutaneous delivery. In still another embodiment, the pharmaceutical carrier may be suitable for topical delivery.

The pharmaceutical composition in one embodiment comprises hyaluronic acid and an alkalinizing agent, optionally in a pharmaceutically acceptable carrier or diluent. In one embodiment, a solution of hyaluronic acid is prepared at a concentration of 1.5% (wt./wt.) in a suitable carrier, such as sterile water. Suitable carriers include Water for Injection (WFI) or physiologically buffered saline. The solution is buffered to a pH of about 8.0 to 10.0, e.g. a pH of 8.5±0.5, for example, using sodium phosphate dibasic heptahydrate and sodium phosphate monobasic monohydrate. The pH adjusted solution may be filled into syringes or other suitable dispensing units. The final product may be sterilized using an acceptable sterilization process, such as ethylene oxide sterilization.

Also provided is a pharmaceutical composition for reducing scar formation at a wound site comprising an effective amount of an alkalinizing agent to raise pH at the wound site and inactivate TGF-β at the wound site and a pharmaceutically acceptable carrier. The raised pH at the wound site may be in the range of about 8.0 to 10.0; about 8.5 to 10.0; about 9.0 to 10.0; about 8.5; or e.g., a pH of about 9.2 to 9.8. The composition may be in a form of an injection solution, and the alkalinizing agent may be present in a concentration of about 0.1 to 1 mEq/0.1 cc of purified water. The hyaluronic acid may be provided in the pharmaceutical composition for administration to the wound site, or it may be administered separately in a pharmaceutically acceptable carrier.

Alkalinizing agents are used to adjust the pH of the composition to an alkaline pH. In order to achieve a target pH, a solution of hyaluronic acid and an alkalinizing agent may be treated with a suitable acid, such as hydrochloric acid (HCl) to adjust the pH of the solution. Alkalinizing agents used in the pharmaceutical compositions include but are not limited to sodium bicarbonate, sodium hydroxide, potassium hydroxide, tromethamine (THAM), acetazolamide (Diamox), sodium citrate, potassium citrate, phosphate salts (potassium phosphate, sodium acid phosphate, and tribasic sodium phosphate), and sodium lactate. Preferred alkalinizing agents include mixtures of sodium phosphate dibasic and sodium phosphate monobasic, sodium bicarbonate, sodium hydroxide and potassium hydroxide. Sodium phosphate dibasic and sodium phosphate monobasic hydrates may be used as well as the anhydrous reagents. Sodium phosphate dibasic heptahydrate and sodium phosphate monobasic monohydrate are used in one embodiment.

The pH of the pharmaceutical compositions is preferably alkaline or greater than pH 7. The pH range which effectively reduces scar formation, namely, which does not activate TGF-β and alkalinizes the wound, may be, e.g. about 8.0 to 10.0, about 8.0 to 9.0, or about 9.0 to 10.0, or in another embodiment, about 9.2 to 9.8. In one embodiment, the pH of the compositions is about 8.5.

Methods for reducing scar formation during the wound healing process by increasing the pH at the wound site are provided. TGF-β is known to play an important role in the scar formation process of the wound. To inactivate TGF-β, the wound should be alkalinized. To easily alkalinize the wound, in one exemplification, an alkalinizing agent such as sodium bicarbonate, NaOH or KOH in a concentration of 1 mEq (1 cc)/distilled water 10 cc is injected to the dermis tissue of the wound or applied topically to directly control pH of the wound, thereby reducing the scar formation of the wound. Hyaluronic acid may be administered in combination or alternation with the alkalinization agent. Also, alkalinizing agents, such as sodium bicarbonate, NaOH and KOH can reduce fibrosis in the process of tissue regeneration or healing, by controlling pH (alkalinization) of the regeneration or healing spot. Thus, in the method for reducing scar formation at a wound site, an effective amount of an alkalinizing agent is administered to the wound site to raise pH at the wound site so as to inactivate TGF-β at the wound site and allow the wound site to heal thereby reducing scar formation at the healing site. The alkalinizing agent may be injected into the dermis tissue of the wound site, or may be administered topically. In particular, the alkalinizing agent is e.g., sodium bicarbonate, sodium hydroxide, potassium hydroxide, tromethamine (THAM), acetazolamide (Diamox), sodium citrate, potassium citrate, phosphate salts or sodium lactate. Alkalinizing agents may be used in combination or alternation with hyaluronic acid. Thus, for example, hyaluronic acid may be included in the composition with the alkalization agent, or may be administered separately, for example in an aqueous solution.

Also provided is a kit for reducing scar formation at a wound site that includes for example, at least one container containing an effective amount of an alkalinizing agent to raise pH at the wound site and inactivate TGF-β at the wound site and a pharmaceutically acceptable carrier, and may contain one medical grade occlusive sheet. For example, the raised pH at the wound site may be about 8.5 to 10.0 or about 9.2 to 9.8. The container may also include hyaluronic acid. The composition may be in a form of an injection or topical solution. The alkalinizing agent may be present in a concentration of about 0.1 to 1 mEq/0.1 cc of purified water, in particular, the alkalinizing agent may be sodium bicarbonate, sodium hydroxide, potassium hydroxide, tromethamine (THAM), acetazolamide (Diamox), sodium citrate, potassium citrate, phosphate salts (potassium phosphate, sodium acid phosphate, and tribasic sodium phosphate) or sodium lactate. The kit may further include written instructions on the use of the kit for reducing scar formation. The kit may include a formulation of hyaluronic acid at a pH of, e.g., about 8.5-10.0 which is in the form of an implant, e.g. for insertion into a wound site, or a body cavity, for example, following ear, nose and/or throat surgery.

Exemplary concentrations and amounts of the various reagents are provided in Tables 1 and 2 below:

TABLE 1

(pH value)

|  | 0.05 mEq | 0.1 mEq | 0.5 mEq | 1.0 mEq |
|---|---|---|---|---|
| NaHCO$_3$ | 8.83 | 9.22 | 9.82 | 10.36 |
| KOH | 8.56 | 9.40 | 9.74 | 10.51 |
| NaOH | 8.55 | 9.38 | 9.87 | 10.50 |

TABLE 2

(mg per 10 ml of distilled water)

|  | 0.05 mEq | 0.1 mEq | 0.2 mEq | 0.5 mEq | 1.0 mEq |
|---|---|---|---|---|---|
| NaHCO$_3$ | 0.020 | 0.040 | 0.080 | 0.200 | 0.400 |
| KOH | 0.028 | 0.056 | 0.112 | 0.280 | 0.560 |
| NaOH | 0.042 | 0.084 | 0.168 | 0.420 | 0.840 |

Those with skill in the art can readily determine concentration and amount of each reagent in inducing the alkaline pHs 8.5-10 at a wound site.

The methods and compositions provided herein can be used in a wide range of applications including for the treatment of wounds and scars, such as hypertrophic and keloid scars. The compositions and methods described herein are used for the management of existing and new hypertrophic and keloid scars resulting from burns, trauma, surgery, laser abrasion, chemical peels and other trauma, and as an adjunct to aid in the natural healing process. The pharmaceutical compositions and methods also may be used in plastic surgery applications.

The compositions described herein can be administered to a wound site by any appropriate route, for example, parenterally, intradermally, subcutaneously, intramuscularly or topically, in forms of solution, suspension, cream, lotion, ointment, gel and the like. Solutions or suspensions used for parenteral, intradermal, subcutaneous, intramuscular or topical application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminctetraacetic acid and agents for the adjustment of tonicity such as sodium chloride or dextrose. The parental preparation can be enclosed in ampoules, disposable syringes or multiple dose vials made of glass or plastic. For application topically to the wound site, the instant composition can be formulated as a suitable ointment containing the alkalinizing agent suspended or dissolved in, for example, a mixture with one or more of the following: mineral oil, liquid petrolatum, white petrolatum, propylene glycol, polyoxyethylene polyoxypropylene compound, emulsifying wax and water. For a suitable lotion or cream, the alkalinizing agent can be suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water. A typical topical dose of the alkalinizing agent will range from 0.1-4.0% wt/wt in a suitable carrier.

In one embodiment, the method comprises injecting or otherwise administering sodium bicarbonate or other alkalinization agent, together or in alternation with hyaluronic acid, to the dermis tissue of a wound, for example, with a syringe to directly control pH of the wound site, to alkalinize the wound and inactivate TGF-β. The agent for reducing scar formation can be clinically and immediately applied to the treatment of a tylosis scar, keloid, etc., and can be used to treat fibrosis diseases.

The hyaluronic acid formulation, in one embodiment, is administered to a wound site as a medical device, to act as an implant or stent to be placed partially or wholly within a patient's body for example at the wound site.

The hyaluronic acid formulation optionally is a space-occupying gel for medical use, which can control minimal bleeding following Ear, Nose and Throat surgery, to separate and prevent adhesions between mucosal surfaces in the nasal cavity, as an adjunct to aid in the natural healing process during the postoperative period. Thus, in one embodiment the hyaluronic acid formulation is administered to a cavity in the ear, nose or throat, for example, the inner ear, outer ear and nasal passages, optionally after surgery, to promote wound healing.

In one embodiment, a solution of sodium hyaluronate with a molecular weight of about 600,000 to 1,100,000 Daltons, or about 750,000 to 1,100,000 Daltons, or about 800,000 to 1,100,000 Daltons, at a concentration of 1.5% (wt./wt.) is buffered to increase the pH for example, to a pH of 8.5±0.5, using for example, sodium phosphate dibasic, heptahydrate and sodium phosphate monobasic, monohydrate. The pH adjusted solution may aseptically be filled into syringes or other suitable dispensing units, such as a 3 ml hypak unit with a plunger stopper and a syringe label, which can be sealed into a container and labelled. The syringe may include a tip cap for dispensing the product on a wound. The final product may be sterilized using an acceptable sterilization process, such as ethylene oxide sterilization. An exemplary formulation is shown below:

Sodium hyaluronate: 1.5%±0.1%;
Molecular weight sodium hyaluronate: 600,000 to 1,100,000 Daltons;
pH: 8.5±0.5; and
Osmolality 149 mOsm/kg.

The final product can be subjected to an ethylene oxide sterilization process.

Optionally a formulation is provided which is a gel which is a sodium hyaluronate based buffered solution at pH 8.5+/−0.5.

Optional Therapeutic Agents

In some embodiments, the composition may further include therapeutic agents, or such therapeutic agents may be administered in combination or alternation with the compositions. Thus, the alkalinizing agent and the hyaluronic acid may be administered in combination with a therapeutic agent, such as an anesthetic agent, a pain reliever, an anti-inflammatory agent, an anti-infective agent and/or an antibiotic agent. Optionally, the composition is formulated to permit slow release of the agent, for example from a hyaluronic acid gel. Higher molecular weight hyaluronic acid may be used, such as a molecular weight of at least 760,000 or 1,000,000, to allow controlled release, e.g., over days, weeks or months.

Examples of agents include non-steroidal anti-inflammatory drugs (NSAIDs), such as aspirin, ibuprofen, nabumetone and naproxen. Other examples include acetamenophin. Anesthetics such as lidocaine may be used.

Antibiotics, for example one, two or three in combination may be used, such as neomycin, bacitracin and polymyxin, alone or in combination.

The present invention is described more specifically by the following non-limiting Examples.

EXAMPLES

Comparative Example 1

Alkaline Solution (pH 8.5)

Preparation

Solution A was 8.4% sodium bicarbonate injection solution purchased from Jeil Pharm. Co., Ltd., Seoul, Korea and adjusted to have pH 7.0 by adding 1N NaOH solution and 1N HCl solution. Solution B was sodium bicarbonate solution having pH 8.5 which was prepared by adjusting the pH of solution A to a pH of 8.5 with the addition of 1N NaOH solution and 1N HCl solution.

Experimentation

In Vitro

WS1 cells that showed more than 95% viability in trypan blue test were selected, thawed from liquid nitrogen, and then grown in 75 cc flask (T75) to form 80% monolayer (about $6 \times 10^6$/T75) on MEM medium (10% FBS). The detection was performed on 24-well plate at the concentration of 10,000 and was repeated three times on each sample. Each well ($10^4$ cells/well) in a 24-well plate containing 3.6 ml of cell suspension was inoculated with solution A or solution B and cultured at 37° C. for 24 hours. The number of cells was counted using hemocytometer 3, 5, 7, and 9 days after the inoculation. The results are shown in FIG. 1.

Figure 1:
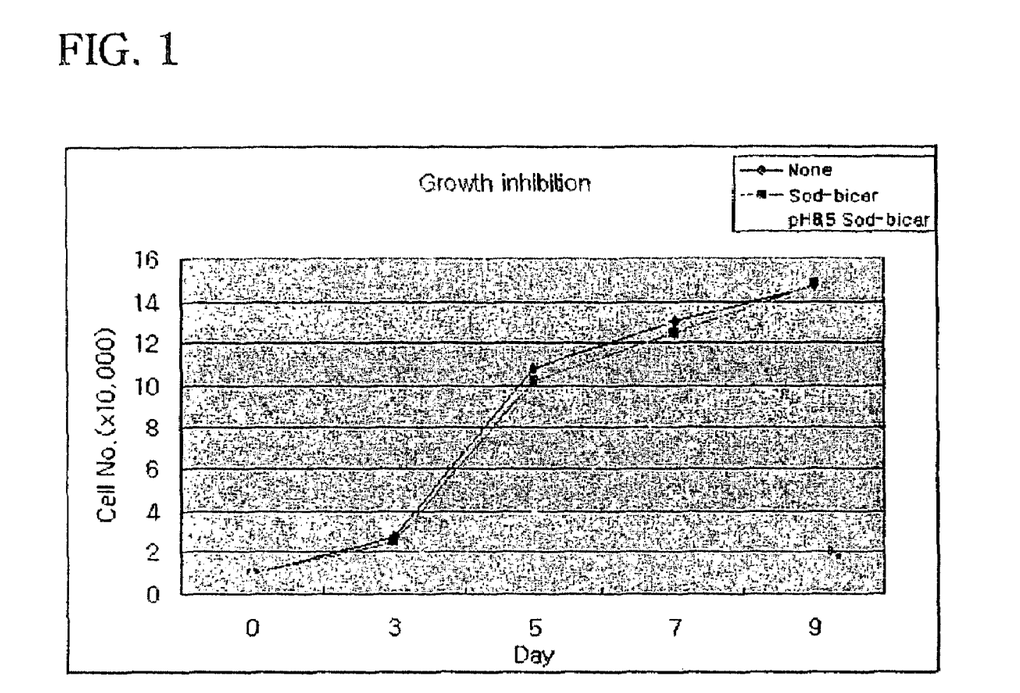
FIG. 1 shows the effect of pH 8.5 sodium bicarbonate solution on inhibiting in vitro cell growth (None=DPBS solution; Sod-bicar 8.4% sodium bicarbonate injection solution; pH 8.5 Sod-bicar=pH 8.5 sodium bicarbonate injection solution).

It can be seen from FIG. 1 that the effect of the solution B on inhibiting cell growth is greater than that of the solution A.

In Vivo

Figure 2:
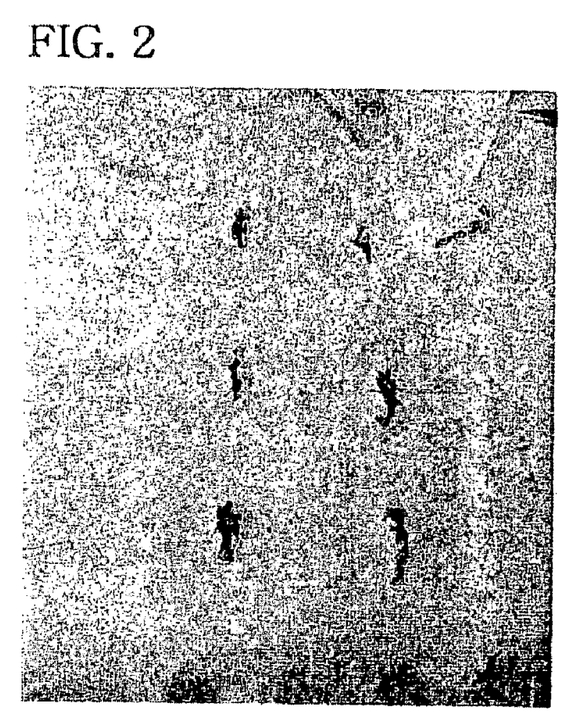
FIG. 2 shows the wounded sites on dorsal region of the test rats.
Figure 3:
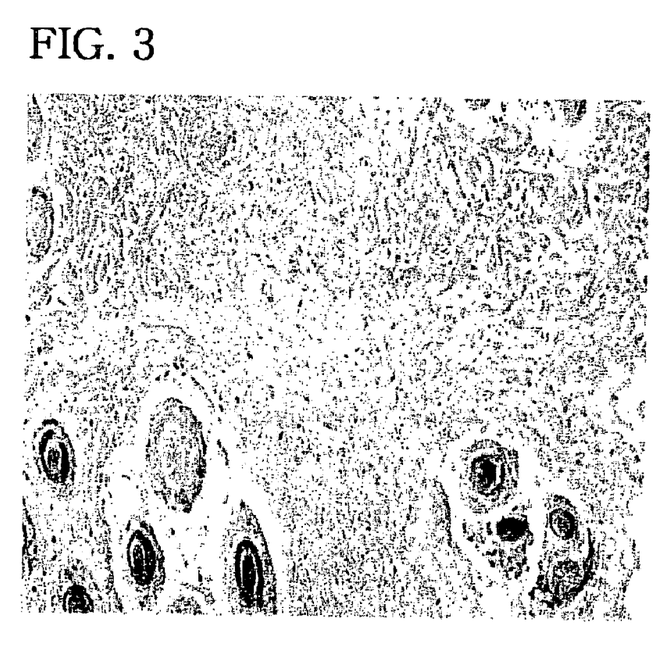
FIG. 3 is a MT staining photograph of the tissue treated in vivo with a sodium bicarbonate solution having a pH of 7.0.
Figure 4:
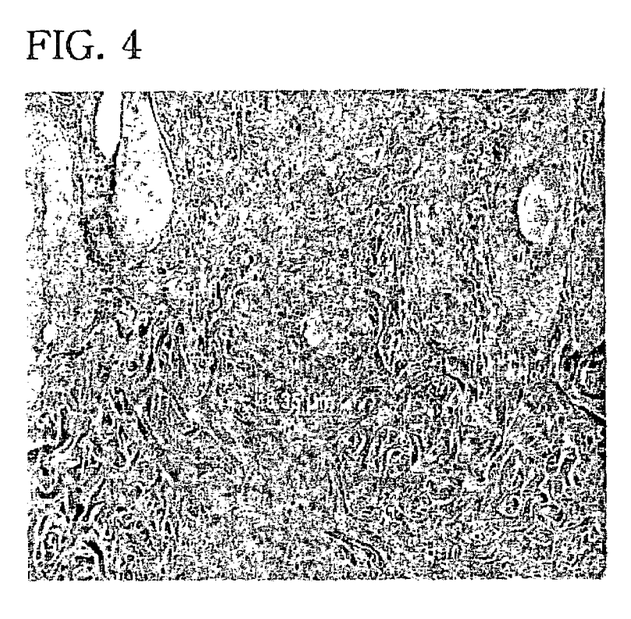
FIG. 4 is a MT staining photograph of tissues treated in vivo with a sodium bicarbonate solution having a pH of 8.5.

Nine female Sprague-Dawley rats weighing 280-300 g were shaved on their dorsal regions and divided into 3 groups (3 rats each group). As shown in FIG. 2, six dorsal sites were wounded (length 1 cm) with surgical scissors and sutured. Three wounds at the left side were treated with 0.5 cc/wound of the solution A and those at the right side were treated with 0.5 cc/wound of the solution B. Tissues were separated from the wound sites 2, 4, and 6 weeks after the injection, embedded into paraffin block, and MT stained. FIGS. 3 and 4 show the results obtained 2 weeks after treatment with solutions A and B, respectively.

It can be seen from the results that the wound sites treated with the solution B have substantially less scar, whereas the wound sites treated with the solution A have visible scars.

Comparative Example 2

Hyaluronic Acid Solution

Preparation

Solution A was DPBS (Dulbecco's Phosphate Buffer Saline, Invitrogen Corp.). Solution B was prepared by dissolving hyaluronic acid in the solution A.

Experimentation

In Vitro

WS1 cells that showed more than 95% viability in trypan blue test were selected, thawed from liquid nitrogen, and then grown in 75 cc flask (T75) to form 80% monolayer (about $6\times10^6$/T75) on MEM medium (10% FBS). The detection was performed on 24-well plate at the concentration of 10,000 and was repeated three times on each sample. Each well ($10^4$ cells/well) in a 24-well plate containing 3.6 ml of cell suspension was inoculated with DPBS solution A or hyaluronic acid solution B and cultured at 37° C. for 24 hours. The number of cells was counted using hemocytometer 3, 5, 7, and 9 days after the inoculation. The results are shown in FIG. 5.

Figure 5:
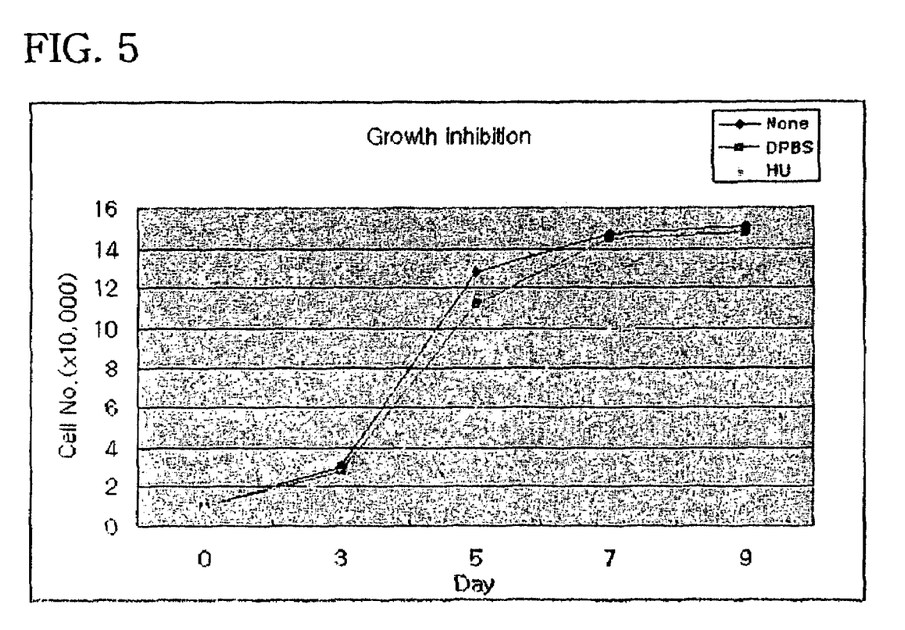
FIG. 5 shows the effect of hyaluronic acid solution on inhibiting in vitro cell growth.

It can be seen from FIG. 5 that the effect of the solution B on inhibiting cell growth is greater than that of the solution A.

In Vivo

Figure 6:
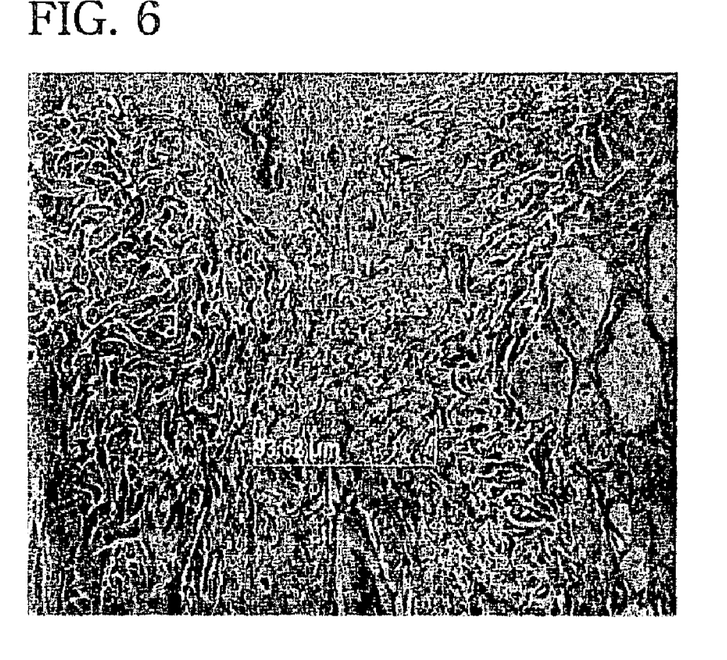
FIG. 6 is a MT staining photograph of the tissue treated in vivo with DPBS.
Figure 7:
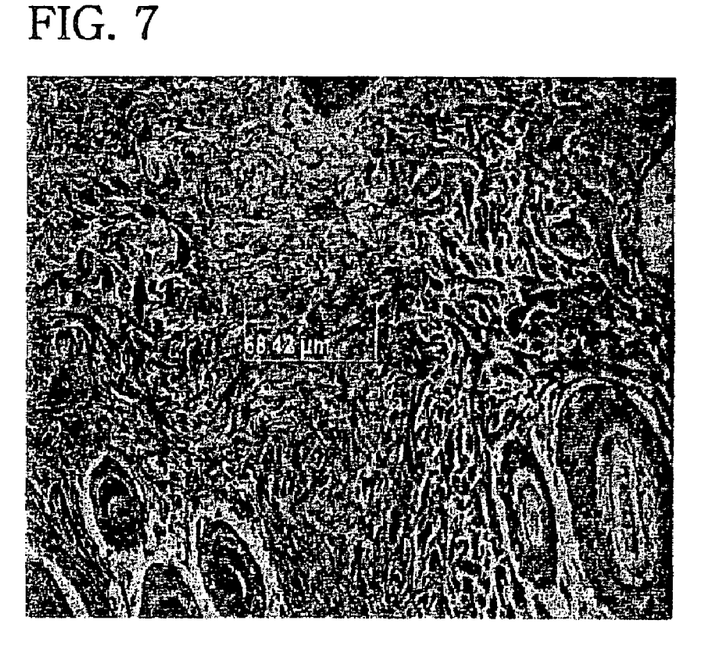
FIG. 7 is a MT staining photograph of the tissue treated in vivo with hyaluronic acid solution.

Nine female Sprague-Dawley rats weighing 280-300 g were shaved on their dorsal regions and divided into 3 groups (3 rats each group). As shown in FIG. 2, six dorsal sites were wounded (length 1 cm) with surgical scissors and sutured. Three wounds at the left side were treated with 0.5 cc/wound of the solution A and those at the right side were treated with 0.5 cc/wound of the solution B. Tissues were separated from the wound sites 2, 4, and 6 weeks after the injection, embedded into paraffin block, and MT stained. FIGS. 6 and 7 show the results obtained 2 weeks after treatment with solutions A and B, respectively.

It can be seen from the results that the wound sites treated with the solution B have less scar formation, whereas the wound sites treated with the solution A have visibly much scars.

Example 1

Alkaline Hyaluronic Acid Solution (pH 8.5)

Preparation

Solution A was prepared by dissolving hyaluronic acid (Sigma Aldrich) in DPBS (Invitrogen Corp.) at a concentration of 25 mg/ml and adjusting the pH as 7.0 with the addition of 1N NaOH and 1N HCl. Solution B was prepared by adjusting the pH of the solution A as 8.5 with the addition of 1N NaOH and 1N HCl.

Experimentation

In Vitro

WS1 cells that showed more than 95% viability in trypan blue test were selected, thawed from liquid nitrogen, and then grown in 75 cc flask (T75) to form 80% monolayer (about $6\times10^6$/T75) on MEM medium (10% FBS). The detection was performed on 24-well plate at the concentration of 10,000 and was repeated three times on each sample. Each well ($10^4$ cells/well) in a 24-well plate containing 3.6 ml of cell suspension was inoculated with pH 7.0 hyaluronic acid solution A or pH 8.5 hyaluronic acid solution B and cultured at 37° C. for 24 hours. The number of cells was counted using hemocytometer 3, 5, 7, and 9 days after the inoculation. The results are shown in FIG. 8.

Figure 8:
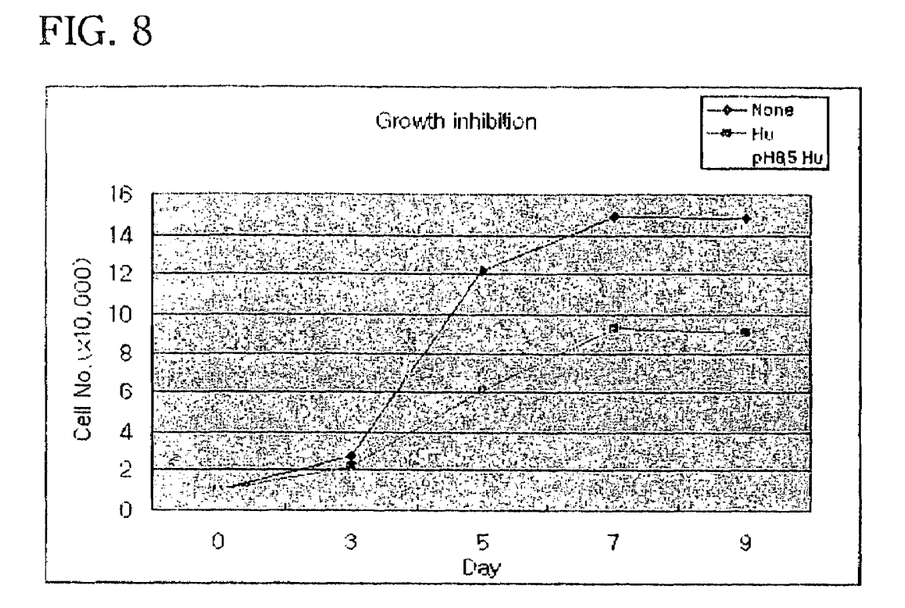
FIG. 8 shows the effect of a pH 8.5 hyaluronic acid solution on inhibiting in vitro cell growth.

It can be seen from FIG. 8 that the effect of the solution B on inhibiting cell growth is highly greater than that of the solution A.

In Vivo

Figure 9:
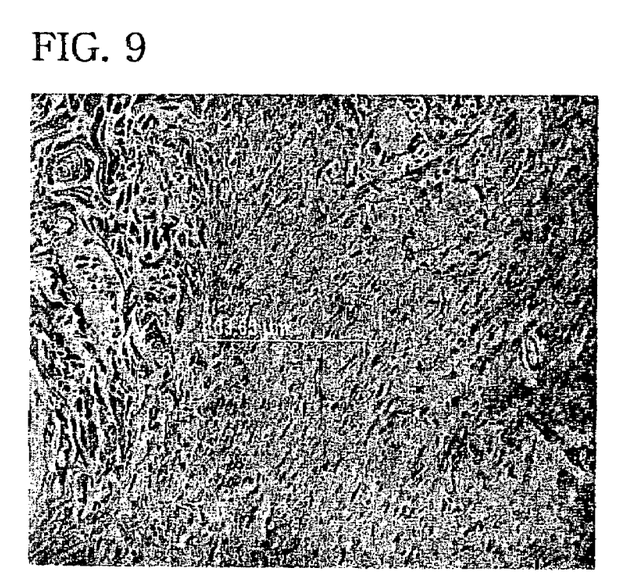
FIG. 9 is a MT staining photograph of tissues treated in vivo with hyaluronic acid solution.
Figure 10:
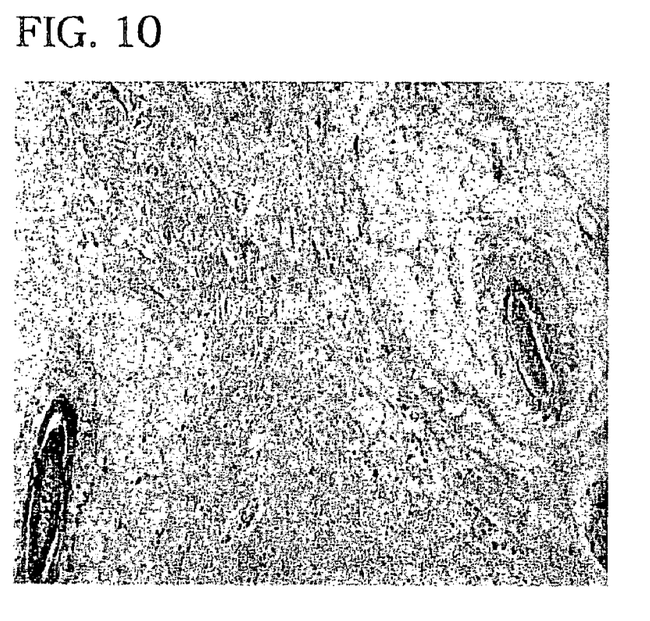
FIG. 10 is a MT staining photograph of the tissue treated in vivo with pH 8.5 hyaluronic acid solution.

Nine female Sprague-Dawley rats weighing 280-300 g were shaved on their dorsal regions and divided into 3 groups (3 rats each group). As shown in FIG. 2, six dorsal sites were wounded (length 1 cm) with surgical scissors and sutured. Three wounds at the left side were treated with 0.5 cc/wound of the solution A and those at the right side were treated with 0.5 cc/wound of the solution B. Tissues were separated from the wound sites 2, 4, and 6 weeks after the injection, embedded into paraffin block, and MT stained. FIGS. 9 and 10 show the results obtained 2 weeks after treatment with solutions A and B, respectively.

It can be seen from the results that the wound sites treated with the solution B have substantially no scar, whereas the wound sites treated with the solution A have noticeable scars.

Example 2

Alkaline Hyaluronic Acid Solution (pH 8.5)

Preparation

Solution A was prepared by adjusting pH of 8.4% sodium bicarbonate injection solution (Jeil Pharma, Co., Ltd., Seoul, Korea) as 8.5 with the addition of 1N NaOH solution and 1N HCl solution. Solution B was prepared by dissolving hyaluronic acid (Sigma Aldrich) in DPBS (Invitrogen Corp.) at a concentration of 25 mg/ml and adjusting the pH as 8.5 with the addition of 1N NaOH and 1N HCl solution.

Experimentation

In Vitro

WS1 cells that showed more than 95% viability in trypan blue test were selected, thawed from liquid nitrogen, and then grown in 75 cc flask (T75) to form 80% monolayer (about $6\times10^6$/T75) on MEM medium (10% FBS). The detection was performed on 24-well plate at the concentration of 10,000 and was repeated three times on each sample. Each well ($10^4$ cells/well) in a 24-well plate containing 3.6 ml of cell suspension was inoculated with pH 8.5 sodium bicarbonate solution A or pH 8.5 hyaluronic acid solution B and cultured at 37° C. for 24 hours. The number of cells was counted using hemocytometer 3, 5, 7, and 9 days after the inoculation. The results are shown in FIG. 11.

Figure 11:
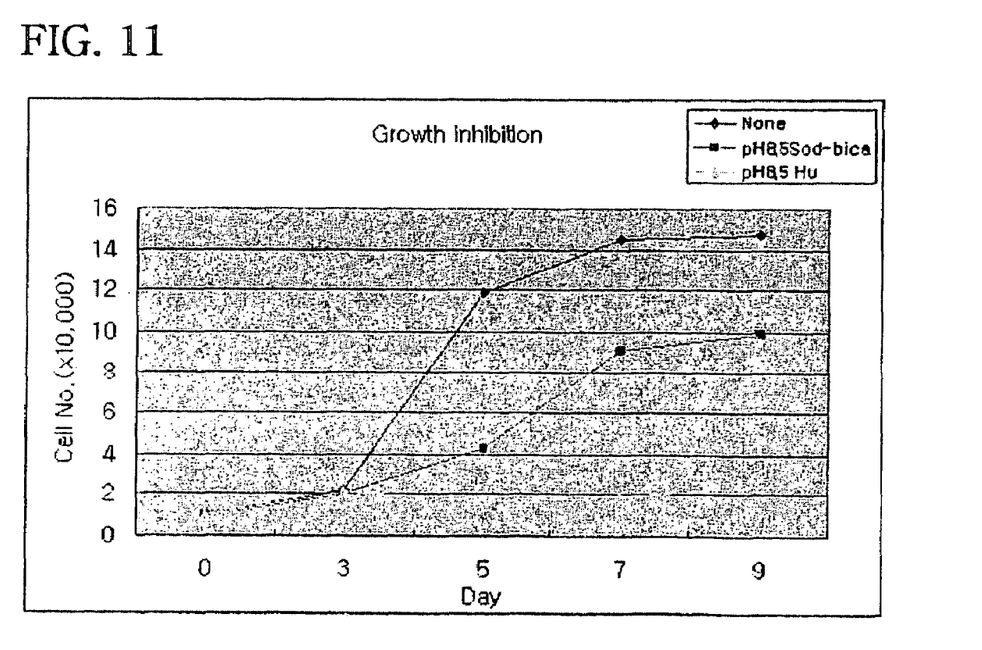
FIG. 11 shows the effect of pH 8.5 sodium bicarbonate solution on inhibiting the in vitro cell growth.

It can be seen from FIG. 11 that the effect of the solution B on inhibiting cell growth is highly greater than that of the solution A.

In Vivo

Figure 12:
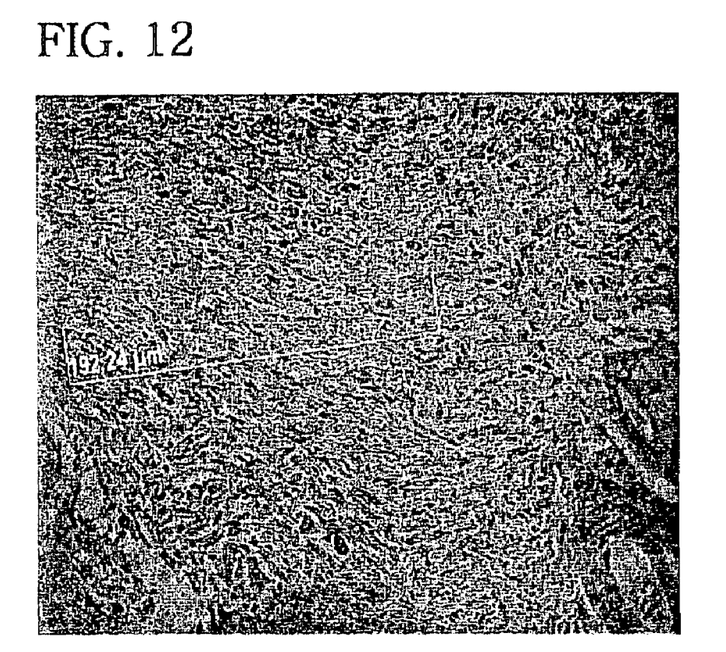
FIG. 12 is a MT staining photograph of the tissue treated in vivo with pH 8.5 sodium bicarbonate solution.
Figure 13:
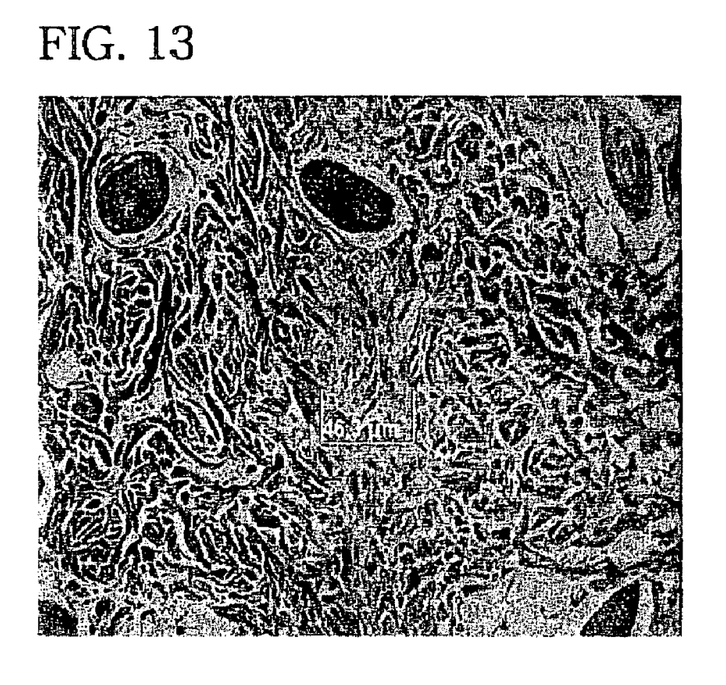
FIG. 13 is a MT staining photograph of the tissue treated in vivo with pH 8.5 hyaluronic acid solution.

Nine female Sprague-Dawley rats weighing 280-300 g were shaved on their dorsal regions and divided into 3 groups (3 rats each group). As shown in FIG. 2, six dorsal sites were wounded (length 1 cm) with surgical scissors and sutured. Three wounds at the left side were treated with 0.5 cc/wound of the solution A and those at the right side were treated with 0.5 cc/wound of the solution B. Tissues were separated from the wound sites 2, 4, and 6 weeks after the injection, embedded into paraffin block, and MT stained. FIGS. 12 and 13 show the results obtained 2 weeks after treatment with solutions A and B, respectively.

It can be seen from the results that the wound sites treated with the solution B have substantially no scar, whereas the wound sites treated with the solution A have noticeable scars.

Consequently, it is evident that the composition consisting of alkalinizing agent and hyaluronic acid and having alkaline pH shows synergism in inhibiting scar formation in wound region over each of hyaluronic acid composition having pHs less than 7 or alkalinizing agent individually.

What is claimed is:

1. A method for reducing scar formation at a wound site comprising administering to the wound site an effective amount of a composition consisting essentially of: hyaluronic acid, or the sodium salt thereof; and an alkalinizing agent in an amount sufficient to raise the pH of the wound site, to allow the wound site to heal and thereby reduce scar formation at the site, wherein the composition has an alkaline pH of about 8.5 to 10.

2. The method of claim 1, wherein the composition further comprises a pharmaceutically acceptable carrier.

3. The method of claim 2, wherein the composition is buffered.

4. The method of claim 1, wherein the composition is administered to the wound site by topical administration to the wound.

5. The method of claim 1, wherein the alkalinizing agent is selected from a group consisting of sodium bicarbonate, sodium hydroxide, potassium hydroxide, tromethamine (THAM), acetazolamide (Diamox), sodium citrate, potassium citrate, potassium phosphate, dibasic sodium phosphate, tribasic sodium phosphate, and sodium lactate.

6. The method of claim 1, wherein the alkalinizing agent is sodium bicarbonate, sodium hydroxide, or potassium hydroxide.

7. The method of claim 2, wherein the pharmaceutically acceptable carrier is suitable for intradermal delivery, subcutaneous delivery, body cavity delivery or topical delivery.

8. The method of claim 1, wherein the composition is administered to a body cavity of the ear, nose or throat, optionally after surgery.

9. The method of claim 2, wherein the concentration of hyaluronic acid is between 0.5% to 5% (wt./wt.).

* * * * *